(12) United States Patent
Egalon (10) Patent No.: US 8,909,004 B2
(45) Date of Patent: Dec. 9, 2014

(54) SIDE ILLUMINATED MULTI POINT MULTI PARAMETER

(71) Applicant: Claudio Oliveira Egalon, Los Angeles, CA (US)

(72) Inventor: Claudio Oliveira Egalon, Los Angeles, CA (US)

(*) Notice: Subject to any disclaimer, the term of this patent is extended or adjusted under 35 U.S.C. 154(b) by 0 days.

(21) Appl. No.: 13/892,274

(22) Filed: May 11, 2013

(65) Prior Publication Data

US 2013/0248697 A1    Sep. 26, 2013

Related U.S. Application Data

(63) Continuation of application No. 12/697,233, filed on Jan. 30, 2010, now Pat. No. 8,463,083.

(60) Provisional application No. 61/148,564, filed on Jan. 30, 2009.

(51) Int. Cl.
| | | |
|---|---|---|
| G02B 6/00 | (2006.01) | |
| G01F 23/292 | (2006.01) | |
| G01N 21/17 | (2006.01) | |
| G01N 21/64 | (2006.01) | |
| G01D 5/353 | (2006.01) | |
| G01N 21/77 | (2006.01) | |
| G01N 21/63 | (2006.01) | |

(52) U.S. Cl.
CPC ........ *G01N 21/17* (2013.01); *G01N 2021/7736* (2013.01); *G01N 2021/635* (2013.01); *G01F 23/2927* (2013.01); *G02B 6/00* (2013.01); *G01N 21/7703* (2013.01); *G01N 21/648* (2013.01); *G01N 2021/6484* (2013.01); *G01N 21/645* (2013.01); *G01N 2201/06193* (2013.01); *G01D 5/353* (2013.01)
USPC .......................................................... 385/12

(58) Field of Classification Search
None
See application file for complete search history.

(56) References Cited

U.S. PATENT DOCUMENTS

| | | |
|---|---|---|
| 4,200,110 A | 4/1980 | Peterson et al. |
| 4,447,546 A | 5/1984 | Hirschfeld |
| 4,582,809 A | 4/1986 | Block et al. |
| 4,659,215 A | 4/1987 | Sumida et al. |
| 4,727,247 A | 2/1988 | Johnston |

(Continued)

FOREIGN PATENT DOCUMENTS

| | | |
|---|---|---|
| EP | 0211587 | 2/1987 |
| EP | 0371675 | 6/1990 |

(Continued)

OTHER PUBLICATIONS

Rajesh, M.; Fabrication and Characterization of Polymer Optical Fibers for Smart Sensing and Optical Amplification. Cochin University of Science and Technology, Jul. 2006.

(Continued)

*Primary Examiner* — Sung Pak
(74) *Attorney, Agent, or Firm* — George P. White (57) ABSTRACT

A side illuminated multi point multi parameter optical fiber sensor that requires no sensitive coating is provided. This sensor comprises an optical fiber having at least one removed cladding section as the sensitive region, at least one probing light source that side illuminates the fiber, a power supply, a detector, a signal processor and a display. The sensitive optical fiber is optically affected by the presence of a measurand medium that can fluoresce, phosphoresce, absorb and/or scatter the probing light. This probing light is guided by the fiber core towards a detector which measures the light intensity and this light intensity is correlated with a measurand.

19 Claims, 8 Drawing Sheets

(56) References Cited

U.S. PATENT DOCUMENTS

| | | | |
|---|---|---|---|
| 4,820,016 | A | 4/1989 | Cohen et al. |
| 4,834,496 | A | 5/1989 | Blyler, Jr. et al. |
| 4,909,990 | A | 3/1990 | Block et al. |
| 5,067,815 | A | 11/1991 | Kotrotsios et al. |
| 5,191,206 | A | 3/1993 | Boiarski et al. |
| 5,249,251 | A | 9/1993 | Egalon et al. |
| 5,262,638 | A * | 11/1993 | Egalon et al. ............ 250/227.14 |
| 5,343,550 | A | 8/1994 | Egalon et al. |
| 5,465,311 | A | 11/1995 | Caulfield et al. |
| 5,577,137 | A | 11/1996 | Groger et al. |
| 5,629,515 | A * | 5/1997 | Maekawa ...................... 250/207 |
| 5,701,006 | A | 12/1997 | Schaefer |
| 5,705,834 | A | 1/1998 | Egalon et al. |
| 5,747,348 | A | 5/1998 | Jaduszliwer et al. |
| 6,205,263 | B1 | 3/2001 | Lieberman et al. |
| 6,328,932 | B1 | 12/2001 | Carter et al. |
| 6,671,451 | B1 * | 12/2003 | Sugihara ...................... 385/144 |
| 6,829,073 | B1 * | 12/2004 | Krol et al. ...................... 359/263 |
| 6,917,735 | B2 | 7/2005 | Murgatroyd et al. |
| 6,965,709 | B1 | 11/2005 | Weiss |
| 7,154,081 | B1 | 12/2006 | Friedersdorf et al. |
| 7,170,590 | B2 | 1/2007 | Kishida |
| 7,209,605 | B2 | 4/2007 | Cantin et al. |
| 7,227,123 | B2 | 6/2007 | Kwon et al. |
| 7,244,572 | B1 * | 7/2007 | Schwabacher et al. ......... 435/7.1 |
| 7,260,283 | B2 | 8/2007 | Lieberman et al. |
| 7,268,371 | B2 | 9/2007 | Krames et al. |
| 7,329,857 | B1 | 2/2008 | Weiss |
| 7,369,730 | B2 | 5/2008 | Childers |
| 7,473,906 | B2 | 1/2009 | Egalon |
| 7,539,363 | B2 * | 5/2009 | Bock et al. ...................... 385/12 |
| 7,650,051 | B2 | 1/2010 | Lieberman et al. |
| 7,668,412 | B2 | 2/2010 | Lee et al. |
| 2002/0018629 | A1 | 2/2002 | Lieberman et al. |
| 2003/0231818 | A1 | 12/2003 | Cantin et al. |
| 2004/0105607 | A1 * | 6/2004 | Cardenas-Valencia et al. 385/12 |
| 2004/0223151 | A1 | 11/2004 | Petros et al. |
| 2005/0053344 | A1 | 3/2005 | Lieberman et al. |
| 2005/0074208 | A1 | 4/2005 | Badcock et al. |
| 2006/0147149 | A1 | 7/2006 | Lieberman et al. |
| 2007/0230859 | A1 * | 10/2007 | Bock et al. ...................... 385/12 |
| 2007/0263954 | A1 * | 11/2007 | Hillendahl et al. ............. 385/12 |
| 2007/0286547 | A1 | 12/2007 | Lieberman et al. |
| 2009/0034901 | A1 * | 2/2009 | Takabayashi et al. .......... 385/12 |
| 2009/0103851 | A1 * | 4/2009 | Tsao et al. ...................... 385/12 |
| 2009/0129721 | A1 * | 5/2009 | Chen et al. ...................... 385/12 |
| 2010/0182607 | A1 * | 7/2010 | Chau et al. ..................... 356/445 |
| 2011/0207237 | A1 * | 8/2011 | Sai et al. ........................ 436/518 |
| 2012/0076452 | A1 * | 3/2012 | Kersey et al. ................... 385/12 |

FOREIGN PATENT DOCUMENTS

| | | |
|---|---|---|
| EP | 1079252 | 2/2001 |
| GB | 2213954 | 8/1989 |
| JP | 06-034550 A | 2/1994 |
| JP | 06010636 B2 | 2/1994 |
| JP | 08-226894 A | 9/1996 |
| JP | 10013345 | 1/1998 |
| JP | 11037922 A | 2/1999 |
| JP | 2001-116687 A | 4/2001 |
| JP | 2002148185 A | 5/2002 |
| JP | 2004354348 A | 12/2004 |
| JP | 2005527838 A | 9/2005 |
| WO | 0171316 A2 | 9/2001 |
| WO | WO0171316 | 9/2001 |
| WO | WO03044567 | 5/2003 |
| WO | 03106942 A1 | 12/2003 |
| WO | 2004078044 A1 | 9/2004 |
| WO | 2006116590 A1 | 11/2006 |

OTHER PUBLICATIONS

Warren-Smith, S. C.; Fluorescence-Based Chemical Sensing Using Suspended-Core Microstructured Optical Fibres. University of Adelaide, Australia, School of Chemistry and Physics, Oct. 2010.

Kim, K.T., Kim, D.G., Hyun, W.K., Ki B.H.; Side-Coupled Asymmetric Plastic Optical Fiber Coupler for Optical Sensor Systems. Journal of the Optical Society of Korea, vol. 12, No. 4, pp. 255-261, Dec. 2008.

Ma, J., Bock, W.J.; Reshaping a Sample Fluid Droplet: Toward Combined Performance Enhancement of an Evanescent-wave Fiber-optic Fluorometer. Optics Letters, vol. 32, No. 1, pp. 8, Jan. 1, 2007.

Ma, J., Bock, W.J.; Revolutionizing the Design of an Evanescent-wave-based Fiber-optic Fluorometer. 19th International Conference on Optical Fibre Sensors, Edited by David Sampson, Stephen Collins, Kyunghwan Oh, Ryozo Yamauchi, Proc. of SPIE vol. 7004, 70040N, 2008.

Ma, J., Bock, W.J., Cusano, A.; Insights into Tunnelling Rays: Outperforming Guided Rays in Fiber-Optic Sensing Device. Optics Express, vol. 17, No. 9, pp. 7630, Apr. 27th, 2009.

Ma, J., Chiniforooshan Y., Chen, H., Chen, J., Bock, W. J., Cusano, A.; Rerouting end-face-TIR Capable Rays to Significantly Increase Evanescent Wave Signal Power. Chinese Optics Letters, col. 9(4), 040603 Apr. 10, 2011.

Chen, H., Ma, J., Chen, J., Bock, W.J.; Significant Retrieval of Lost Evanescent Power by Tuning Modes Close-toCutoff with a Gel-Coated Taper. Chinese Optics Letters / vol. 36, No. 11, pp. 2092, Jun. 1, 2011.

Chen, H., Ma, J., Chen, J., Bock, W.J., Cusano, A.; Covering a Fiber Taper with a Refractive Index Matching Gel Residue: A Significant Increase in Evanescent-Wave Signal Sollection Efficiency. Chinese Optics Letters, col. 9, S10701 Jun. 30, 2011.

Chiniforooshan Y., Ma, J., Bock, W.J.; Evanescent-Wave Fiber-Optic Sensor: On Power Transfer From Core-Cladding Interface to Fiber End-Face. Journal of Lightwave Technology, vol. 30, No. 8, Apr. 15, 2012.

Pulido C., Esteban, Ó.; Characterization of Tapered Polymer Optical Fibers Under Side Illumination for Fluorescence Sensing Applications. 21st International Conference on Optical Fiber Sensors. Proc. of SPIE vol. 7753, 775359, 2011.

Pulido C., Esteban, Ó.; Multiple Fluorescence Sensing with Side-Pumped Tapered Polymer Fiber. Sensors and Actuators B: Chemical, vol. 157, Issue 2, pp. 560-564, Oct. 20, 2011.

Aiestaran, P., Dominguez, V., Arrue, J., Zubia, J.; A Fluorescent Linear Optical Fiber Position Sensor. Optical Materials, vol. 31, pp. 1101-1104 2009.

Pulido C., Esteban, Ó.; Improved Fluorescence Signal with Tapered Polymer Optical Fibers Under Side-Illumination. Sensors and Actuators B : Chemical, vol. 146, Issue 1, pp. 190-194, Apr. 2010.

Bunge, C., Kruglov, R., Poisel, H.; Rayleigh and Mie Scattering in Polymer Optical Fibers. Journal of Lightwave Technology, vol. 24, No. 8, Aug. 2006.

Egalon, C.O.; Side Illuminated Optical Fiber Sensor Array for Relative Humidity. PITTCON 2012, Orlando, FL, Mar. 2012.

Egalon, C.O., Matta, M.P., Lavezzari, D.C., Isley, R.Y., Campbell, E.R., Campbell W.H.; New Colorimeter Using a Side Illuminated Optical Fiber. Accepted for publication for PITTCON 2013, Philadelphia, PA, Mar. 2013.

4. C. Pulido and Ó. Esteban, "Improved fluorescence signal with tapered polymer optical fibers under side-illumination", Sensors and Actuators B: Chemical, vol. 146, Issue 1, Apr. 8, 2010, pp. 190-194.

Lieberman et al., "A distributed fiber optic sensor based on cladding fluorescence", J. Lightwave Tech., vol. 8, No. 2, Feb. 1990, pp. 212-220.

Prince et al., "A Readout Scheme Providing High Spatial Resolution for Distributed Fluorescent Sensors on Optical Fibers", Analytical Chemistry, vol. 73, No. 5, Mar. 1, 2001.

Mendoza et al., "Distributed fiber optic chemical sensors for detection of corrosion in pipelines and structural components", SPIE Procedings, vol. 3398, pp. 136, Mar. 1998.

Albin, Sacharia; Bryant, Alvin L.; Egalon, C. O. and Rogowski, R. S., "Injection efficiency from a side excited thin film fluorescent cladding of a circular waveguide", Optical Engineering, vol. 33, No. 4, pp. 1172-1175, Apr. 1994.

A. Bryant ; S. Albin; C. O. Egalon and R.S. Rogowski "Changes in the amount of core light injection for a fluorescent clad optical fiber due to variations in the fiber refractive index and core radius: experimental results", J. Opt. Soc. of America B, vol. 12, No. 5, pp. 904-906, May 1995.

(56) References Cited

OTHER PUBLICATIONS

Fitzpatrick et al., "A novel multi point ultraviolet optical fibre sensor based on cladding luminescence", Meas. Sci. Technol., vol. 14, pp. 1477-1483, 2003.

Dietrich Marcuse, "Launching light into fiber core from sources located on the cladding", Journal of Lightwave Technology, Aug. 1988, p. 1273, vol. 6, No. 8.

Egalon, Claudio O., "Modelling an Optical Fiber Bragg Grating", Ph.D. Dissertation, Old Dominion University, Dec. 1996.

D. F. Merchant, P.J. Scully and N. F. Schmitt in "Chemical tapering of polymer optical fibre", Sensors and Actuators, vol. 76, pp. 365-371, 1999.

M. F. Triola, "Elementary Statistics", 10th Edition, Pearson/Addison Wesley, 2007.

Hach, Master Catalog, 2008-2009.

* cited by examiner

SIDE ILLUMINATED MULTI POINT MULTI PARAMETER

CROSS-REFERENCE TO RELATED APPLICATION

This application claims the benefit of nonprovisional application Ser. No. 12/697,233, filed on Jan. 30, 2010, which in turn claims the benefit of U.S. Provisional Application No. 61/148,564, filed 30 Jan. 2009.

BACKGROUND

1. Field of the Invention

This invention relates generally, to spectroscopic based optical fiber sensors. Particularly, this invention relates to scattering, absorption, colorimetric, fluorescent and phosphorescent based sensors.

2. Description of Prior Art and Other Considerations

Spectroscopic based optical fiber sensors can be used in several applications to detect strain, pressure, temperature, chemical species, turbidity, color and other measurands. Two separate approaches have been used with these types of sensors: the optrode (or optode) and the distributed sensing approach.

Optrodes are the simplest type of optical fiber sensors. An optrode comprises an indicator located at the distal end of the optical fiber and an excitation light source and a detector at the proximal end. The excitation light travels through the fiber and interacts with the indicator, producing a spectral signal (fluorescence, phosphorescence, colorimetric and/or absorption based signal). The signal travels back to the proximal end, is collected by a detector and is correlated with the parameter that is being measured. In this case, the fiber has a single sensitive region at its distal end and serves only as a conduit for the light, which propagates undisturbed from the proximal fiber end to the indicator and back.

In the distributed sensing approach, the entire fiber, or sections of the fiber, acts both as a conduit for the signal and as a sensor. The fiber can be manufactured either with a single monolithic cladding, made sensitive to the parameter being measured, or made with several sensitive cladding sections separated from one another. Regardless of the approach, these sensitive, or reactant regions, can be probed by an excitation light, resulting in a multipoint, quasi distributed, sensing device. Whereas a distributed sensor requires a single fiber strand to make multiple spatial measurements, an optrode requires several fibers. Therefore, the advantage of distributed sensing is that it can make multiple spatial measurements with a single device.

The sensing points of a distributed optical fiber sensor can be probed in two different ways: either axially or transversely; however, transverse probing is judged herein to be a superior mode of operation.

Axial probing is widely used as a means to probe the sensor fiber. In axial probing, light is injected from one end of the fiber, along its axis, and interacts with the surrounding cladding via its evanescent wave tail. The cladding then absorbs the probing light in the evanescent region producing either an absorption, scattering or luminescent signal that can be detected at either end of the fiber.

This type of excitation with respect to axial probing, however, has important disadvantages. For instance, the interaction between the evanescent wave of the excitation light and the sensitive cladding is very weak, requiring expensive instrumentation to detect the resulting signal, such as a high power source, an expensive detection scheme and/or a very long optical fiber. Additionally, depending on the arrangement, the alignment of the light source (such as a laser) with the fiber axis requires careful handling.

Schwabacher et al., international publication number WO 2001/71316 ('316), entitled "One-dimensional Arrays on Optical Fibers," (also, U.S. Pat. No. 7,244,572 issued 17 Jul. 2007) demonstrates a linear array of chemosensors arranged along an optical fiber, with each reactant region in the array being sensitive to a chemical species. Each successive reactant region is separated by a substantially inert region, such as cladding. This substantially inert region must have a minimum length, the preferable length being stated as 250 cm. Publication '316 demonstrates both the axial and transverse methods of excitation, with the axial method being the preferred mode.

In the preferred embodiment, publication '316 employs a narrow axial laser pulse to introduce an excitation light to the optical fiber. Each reactant region is separated by a minimum distance along the fiber, with the region between the reactant regions being substantially inert. This relative long inert section is required by the technology utilized by publication '316, to prevent overlap of fluorescent traces from successive reactant regions. An excitation light from a source (such as a laser, diode laser, gas laser, dye laser, solid state laser, LED, etc) is introduced axially to an optical fiber, with the light then being delivered to the reactant regions.

In order to determine which reactant region, among several or even hundreds, is producing a signal, the time delay between the excitation pulse and return signal must be precisely known and correlated with the distance each particular reactant region is from the source. This determination involves the measuring of time, distance, and wavelength by use of precise instruments such as by the use of an oscilloscope and a photomultiplier tube. This arrangement requires an extremely long length of fiber in order to measure hundreds of species, and thus increases the overall size and complexity of the analyzing device. Furthermore, the precision instruments can increase the overall cost of the instrument significantly.

The excitation light can also be introduced to the reactant regions on the sensing fiber by an excitation fiber or fibers. This also requires the axial introduction of light to the excitation fiber. One excitation fiber per reactant region is required in one embodiment, with each fiber introducing the excitation light transversely to the reactant region of the sensing fiber.

Another embodiment requires the use of beam splitters to deliver the excitation light transversely to the reactant regions. The beam splitting technique make use of expensive high power lasers resulting in a decay of the intensities as more beam splitters divert the excitation light to the sensitive coating.

In another scheme, the excitation (or illumination) fiber is prepared by removing its cladding from small sections along its length, with these sections then being installed adjacent to the reactant regions on a nearby sensing fiber, and allowing its evanescent field to transversely excite the sensing fiber. A disadvantage is that the evanescent field of the excitation fiber is very weak, thus delivering very little power to the sensing fiber. Additionally, other methods of axial and transverse excitation are revealed; however, these methods were, on average, not cost effective.

Although these embodiments of publication '316 are assumably operational, they are limited by complexity, manufacturing expense, and robustness of design. In order to manufacture alternating sections of reactant and inert regions, cladding must be removed only in the reactant regions, leaving intact the remaining inert regions. This alternating removal of cladding increases the expense and complexity of mass production, limiting automation options in manufacture.

Additionally, other techniques utilized in industry require the use of expensive instrumentation such as an optical time domain reflectometer (OTDR). Costing on the order of US $3,000 or more, an OTDR adds considerable expense to any system that uses the axial excitation technique. Also, the wavelengths availability of OTDR systems is limited, restricting the choices of reagents that can be used with the sensor. A further disadvantage of present systems is the interference of the signal detected by the OTDR caused by inadvertent bends and physical irregularities in the waveguide material, either of which can vary the fiber's refractive index. Furthermore, present techniques lack refinement of spatial resolution, on the order of approximately 10 cm. A more refined spatial resolution is needed.

While transverse probing of the sensitive region appears to be a superior technique that can produce a substantial signal, the prior art failed to identify this and other additional advantages. Side illumination, when properly done, can probe very small sections of a sensitive fiber, leading to a sensor with a very high spatial resolution and, consequently, multiple sensing points along the fiber length. For example, a high spatial resolution, of 5 mm can lead to ten sensing points for every 5 cm of fiber resulting in a high density sensor array in a single fiber. High spatial resolution also is desired in applications in which there is a strong variation of the temperature and/or concentration of a chemical species along the length of the optical fiber. The monitoring of chloride ions inside concrete structures, serves as an example of where the sensing can be made at discrete narrow locations along the fiber. Previous endeavors failed to provide a simpler illumination technique that leads to a low cost, rugged, distributed sensor. More importantly, the prior art has failed to recognize that a side illuminated optical fiber sensor without a chemical indicator in its cladding can detect certain parameters.

There are many needs and desires to overcome these and other deficiencies and/or problems in the prior art, as exemplified but not necessarily limited to the following:

a. an inexpensive probing light source that can additionally provide a high spatial resolution to the fiber sensor, on the order of 5 mm or less, enabling the pinpointing of the exact location of detection;

b. a cost effective optical fiber sensor system that uses inexpensive, off the shelf, commercially available devices that can be fabricated by automated means;

c. a flexible device that can be used throughout the infrared, visible, and ultraviolet regions of the electromagnetic spectrum;

d. a rugged sensing device that can be easily aligned and is not affected by outside interference such as bending and ambient light;

e. a generic design that can be adapted to monitor different measurands is needed;

f. an intense, yet, cost effective probing light source for a fluorescent based and absorption based fiber that can produce a strong signal that can be easily detected;

g. a modular sensing system design that can be easily updated with the evolving technology; and h. a sensing system that does not require a chemical indicator immobilized over the surface of the fiber to detect a given measurand.

SUMMARY OF THE INVENTION

These and other problems and needs are successfully addressed and overcome by the present invention. In accordance with the present invention a reversible, rugged, inexpensive, distributed optical fiber sensor with high spatial resolution that uses no chemical indicator is presented. A variation of the active cladding fiber is also presented. The present invention can be used throughout the infrared, visible, and ultraviolet regions of the electromagnetic spectrum. The light source of the present invention provides an intense, yet, cost effective means for probing the environment associated with the fiber and produces a strong signal that can be easily detected. The present invention can be used with different light sources having different wavelengths, each sensitive to a particular parameter that is being measured. The present invention can be continually updated with new probing light sources, new sensors, and new computing codes.

The preferred embodiment of the present invention generally comprises an optical fiber having multiple bare core regions, a probing or excitation light source, a power supply, a detector, a signal processor, and a display. The probing or excitation light source is in direct optical communication with the optical fiber sensing point, but can be either positioned next to the sensing point or further away, such as a collimated light beam several meters of distance, provided it can illuminate this point. The optical fiber can be used as a sensor to determine the measurand of a medium, including such parameters such as environmental color, turbidity, fluorescence, spectral absorption, concentration of chemical species, index of refraction and any other properties that are optically affected, in a monotonic relationship, by these measurands.

The optical fiber sensor is illuminated, from the outside, at an angle, by a probing light from the light source. The probing light interacts with the region associated with the optical fiber and this region, upon being probed, modifies the probing light generating a light signal that is affected by the presence of a measurand. The light signal is coupled into the optical fiber core as a light signal and guided to a detector, which is in axial optical communication with the terminal end of the fiber. The detector correlates the intensity of the light signal with an electric signal. The electric signal is transmitted to the signal processor, and correlated with the measurand (color, turbidity, index of refraction, concentration of chemical species, etc.) that is being measured. The correlated quantity is transmitted and displayed on the display.

Either a portion or the entire area surrounding the core of the optical fiber is sensitive to the environment and/or the chemical species being measured. Unlike the art disclosed by Egalon (U.S. Pat. No. 7,473,906), a sensitive dope is not necessarily required. The resulting sensitive fiber is reversible, consistently returning to a reference intensity signal.

In a preferred configuration, the probing light source is a UV LED, which is positioned adjacent to the optical fiber, and which illuminates its sensitive region. The UV LED is preferred for several reasons, although it is to be understood that other illuminating sources may be employed. Primarily, the preference for choosing the UV LED is that it is an inexpensive and readily available source of excitation light, which decreases manufacturing expense. Secondly, recent LED technology has improved the intensity and decreased the size of the UV LED, allowing for a narrow, intense interrogating light beam. Additionally, the close proximity of the UV LED to the optical fiber allows for an increased intensity of the light signal, enabling the use of an inexpensive detector, such as a silicon photo detector. Finally, the small LED size enables illumination of small regions of the cladding at multiple positions along the fiber length, resulting in multiple independent sensing points with high spatial resolution. The technique also allows for the exact locating of the point of detection in a substance, showing the spatial variation of the measurand along the length of the fiber, with a very high resolution.

An additional embodiment can include a reflector at the second terminus 118 of the optical fiber opposite of the detector, increasing the light signal through redirecting backward propagating modes towards the detector.

Yet another embodiment includes the use of a sensitive optical fiber with a tapered core, generally diverging towards the detector as the light signal propagates from the sensitive region of the optical fiber to the detector. This core configuration has the advantage of coupling more light into the fiber core than the regular optical fiber cylindrical. With a tapered optical fiber, light rays that otherwise would radiate away from the fiber core are coupled as low loss bound modes and propagate for much longer lengths. This fiber can be manufactured using a drawing tower with a tapered glass preform. Alternatively, this fiber can also be manufactured manually by a person skilled in the shaping of glass.

In yet another embodiment, a plurality of light sources are positioned in a linear array along the length of the bare core optical fiber, wherein each light source consecutively, simultaneously, or independently emits a probing light, at an angle, towards the optical fiber core. The length of the array corresponds substantially to the length of the sensing region of the optical fiber. This arrangement is useful for increasing the overall light intensity of the coupled light signal.

Another alternate embodiment uses an illumination optical fiber, instead of an LED light source, to probe the sensing fiber at specific sections. The illumination fiber is fabricated by embedding several dielectric mirrors inside an optical fiber which is deployed along the sensing fiber. Each mirror, positioned at an angle of 45 degrees, is designed to reflect light at a specific wavelength, $\lambda_i$, from a bound mode in the illumination fiber, towards the side of the sensing fiber. These wavelengths, $\lambda_i$, are within the absorption spectrum of the medium associated with the sensing fiber. By varying the wavelength of the input light, it is possible to probe multiple points, at known locations, along the fiber sensor, thus creating an enhanced distributed sensing system.

In this case, light from a broadband light source passes through a monochromator that scans the wavelengths within the absorption spectrum of the sensing fiber associated medium. When the monochromator is tuned to a wavelength $\lambda_i$, only the dielectric mirror tuned to this wavelength couples the light towards the sensitive optical fiber and the illuminated section corresponds to the position of this specific dielectric mirror. The procedure can be repeated for other wavelengths.

An additional embodiment uses an active core optical fiber doped with a substance that amplifies the signal from the sensitive region. This embodiment works in a way similar to that of an optical fiber amplifier. Accordingly, the signal from the sensitive coating is coupled into the fiber core. The active core is then excited by the light modified by the sensitive coating amplifying the original signal. This amplified signal is then guided to the detector. This embodiment is preferred whenever long lengths of fiber are used.

The present invention, and its alternate embodiments, can be used in an environment that contains substances that fluoresce, absorb or scatter light. For example, the concentration of chlorophyll in water can be determined by exciting its fluorescence with a UV light source. The concentration of a substance in a liquid can be determined through color measurements after employing a colorimetric reaction. A chemical species can also be determined using several light sources of different peak wavelengths that coincide with the chemical's absorption signature. Turbidity can be determined by side illuminating the fiber at any wavelength and measuring the intensity of the coupled light.

The present invention is designed to substantially expand the capability of the art disclosed by Egalon (U.S. Pat. No. 7,473,906) and, in the process, further improve optical fiber sensing systems by, primarily, transversely positioning the light source, such as a UV LED or a visible light LED, directly adjacent to or further away from the sensitive region of the sensitive optical fiber. This arrangement increases the intensity of the coupled light signal, decreases complexity and manufacturing costs and, when using LEDs with small sizes, allows for the exact locating of the point of detection in a substance with a high spatial resolution.

DESCRIPTION OF THE PREFERRED EMBODIMENTS

The following detailed description is of the best presently contemplated mode of carrying out the invention. This description is not to be taken in a limiting sense, but is made merely for the purpose of illustrating general principles of the several embodiments of the invention. The detailed description set forth below, in connection with the appended drawings, is intended as a description of presently preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

Figure 1A:
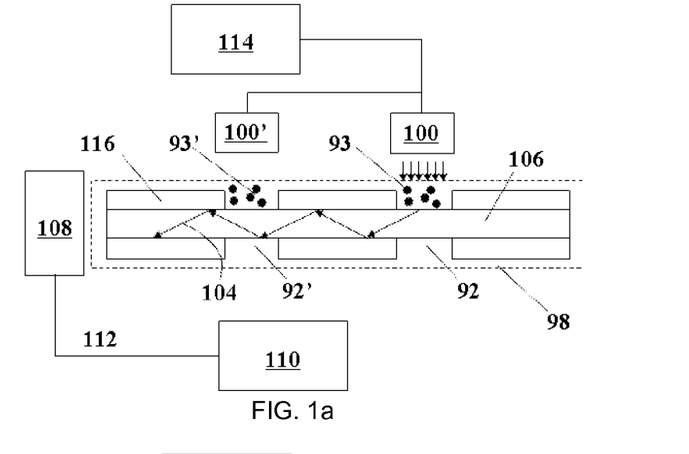
FIG. 1a is a block diagram illustrating the operation of the present invention and its distributed sensing capability in which the analyte is either fluorescent or phosphorescent. In this figure, the probing light source (100), at the right hand side of the figure, is probing an analyte (93) in the measurand associated medium of the sensing fiber (98), in which a portion or portions of the cladding of a commercially available optical fiber have been removed, located in source's corresponding sensing point (92).

A block diagram of the sensing fiber 98 is shown in FIG. 1a. Accordingly, an probing light source 100 illuminates, at an angle, from the outside, a sensing point 92 of the sensing fiber 98. The probing light source 100 has a wavelength capable of producing fluorescence/phosphorescence from the analyte 93 which is in the region of the sensing point 92. Upon illumination from the probing light source 100 (illuminating light shown as arrows), analyte 93, which is nearby the optical fiber core 106, generates fluorescence which is coupled into the optical fiber core 106 as an optical signal 104 in the form of leaky and bound modes. The probing light source 100 is attached to a power supply 114 that provides current to the probing light source 100, which is in optical communication with the optical fiber core 106.

The fluorescence 104, coupled into the optical fiber core 106, is guided to a detector 108, such as a silicon photo-detector, which correlates the light intensity of the fluorescence 104 with an output electrical signal. This electrical signal is transmitted to a signal processor 110, such as a light-meter, via a photo detector cable 112. At the signal processor 110, the signal is amplified and its optical intensity is displayed. The intensity read by the signal processor 110 is then correlated with the concentration of the analyte 93 surrounding the optical fiber core 106.

Figure 1B:
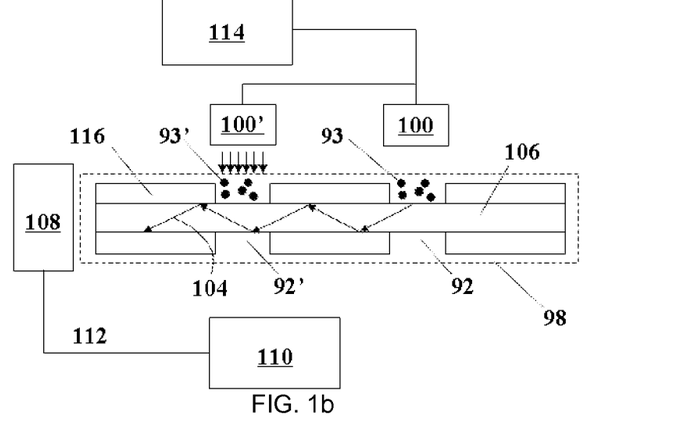
FIG. 1b is a block diagram illustrating the operation of the present invention and its distributed sensing capability in which the analyte is either fluorescent or phosphorescent. In this figure, the probing light source (100') at the left hand side of the figure is probing an analyte (93') in the measurand-associated medium, which measurand-associated medium is located in source's corresponding sensing point (92').

In order to probe a different sensing point 92' of the sensing fiber 98 and to achieve enhanced distributed sensing (see FIG. 1b), the probing light source 100' can be activated separately by the power supply 114 to probe the second sensing point 92' next to the probing light source 100'.

Figure 1C:
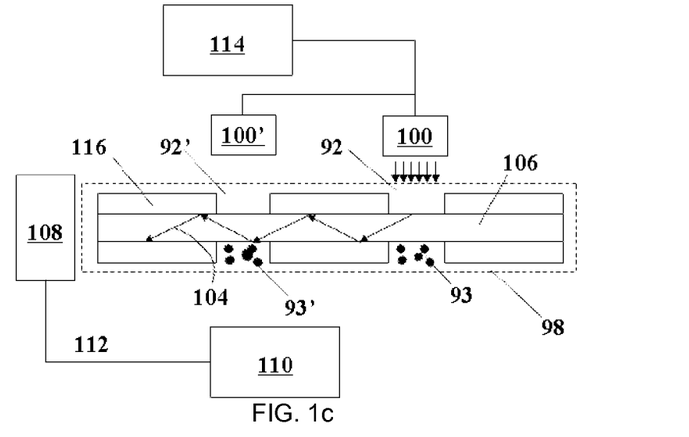
FIG. 1c is a block diagram illustrating the operation of the present invention with the optical fiber core (106) located between the analyte (93) and the probing light source (100).

This configuration can be used either with the analyte 93 between the probing light source 100 and the optical fiber core 106 (FIGS. 1a and 1b) or with the analyte on the other side of the core (FIG. 1c), or the analyte completely or partially surrounding the fiber.

A sensor for chlorophyll (analyte 93) dissolved in water (measurand-associated medium in sensing point 92) is a practical example of the above configuration. Here, chlorophyll fluoresces when illuminated by a probing light source 100 of proper wavelength. This fluorescence couples into the fiber core as an optical signal 104 and its intensity is a measure of the concentration of chlorophyll around the fiber core.

Figure 2A:
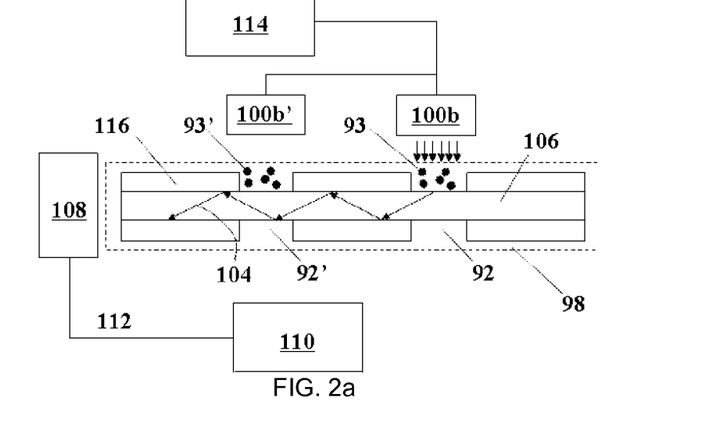
FIG. 2a is a block diagram illustrating the operation of the present invention for which the analyte either absorbs or scatters the radiation coming from the light source. In this figure, the analyte (93) is between the probing light source (100) and the optical fiber core (106).
Figure 2B:
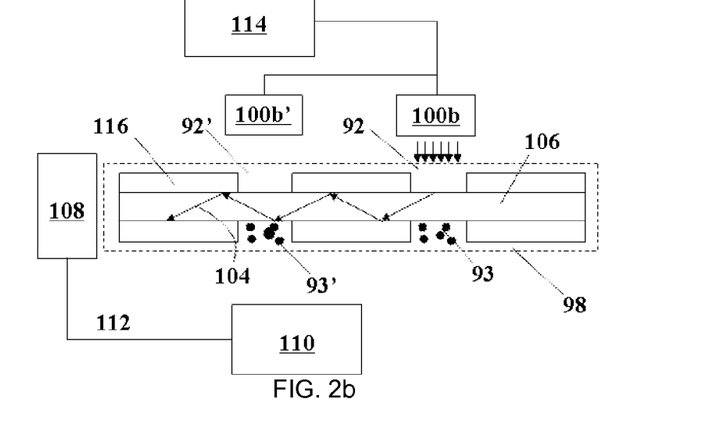
FIG. 2b is a block diagram illustrating the operation of the present invention for which the analyte either absorbs or scatters the radiation coming from the light source. In this figure, the optical fiber core (106) is between the probing light source (100) and the analyte (93).

A similar approach can also be used for absorption, colorimetric and scattered based optical fiber sensors, as shown in FIGS. 2a and 2b. Accordingly, a probing light source 100 illuminates, at an angle, from the outside, the sensing point 92 of the sensing fiber 98. The probing light source 100 has a wavelength capable of being absorbed or scattered by analyte 93 which is next to the fiber sensing point 92. The probing light source 100 is attached to a power supply 114 that provides the current to the probing light source 100 in optical communication with the sensing point 92.

Upon illumination from the probing light source 100 (with the illuminating light shown as arrows), an analyte 93, dissolved in the measurand-associated medium, next to the fiber sensing point 92, and in contact with the optical fiber core 106, absorbs the light from probing light source 100. The remaining light is coupled into the optical fiber core 106 as an optical signal 104 in the form of leaky and bound modes and guided to a detector 108 that reads a light intensity that is related to the concentration of the analyte.

Referring further to FIGS. 2a and 2b, measurand-associated medium, located next to the fiber sensing point 92, can also be the result of a colorimetric reaction between analyte 93 and a chemical reagent. Upon illumination from the probing light source 100b (with the illuminating light shown as arrows), measurand-associated medium, next to the fiber sensing point 92, in contact with the optical fiber core 106, absorbs the light from probing light source 100b. The remaining light is coupled into the optical fiber core 106 as an optical signal 104, in the form of leaky and bound modes, and guided to a detector that reads a light intensity that is related to the concentration of the analyte.

Again referring to FIGS. 2a and 2b, measurand-associated medium, next to fiber sensing point 92, can contain particles that scatter the light from probing light source 100b (with the illuminating light shown as arrows). This scattered light is coupled into the optical fiber core 106 as an optical signal 104, in the form of leaky and bound modes, and guided to a detector that reads a light intensity that is related to a measurand, such as turbidity.

In any case, the light from the probing light source 100 is modified by the surrounding environment, is coupled into the optical fiber core 106 as an optical signal 104, in the form of leaky and bound modes, and is guided to a detector 108, such as a silicon photo-detector, which correlates the light intensity of the absorbed light to an output electrical signal. This electrical signal is transmitted to a signal processor 110, such as a light-meter, via a photodetector cable 112. At the signal processor 110, the signal is amplified and its optical intensity is displayed. The intensity read by the signal processor 110 is then correlated with the concentration of the chemical species either surrounding the sensing fiber 98 or initially present in the original un-reacted medium. As before, distributed sensing can be achieved by probing sensing point 92' of the fiber with another probing light source 100'. Similarly, this configuration can also be used either with the analyte 93 or the reacted measurand-associated medium in sensing point 92 between the probing light source 100 and the optical fiber core 106, as shown in FIG. 2a, or with the analyte or reacted medium on the other side of the core as shown in FIG. 2b.

The configuration illustrated in FIGS. 2a and 2b can be used as a colorimeter to detect different chemical species, as a turbidity meter to detect turbidity and as a refractometer to detect the level of a given liquid.

There are several colorimetric reactions that can be used to detect different parameters such as, but not limited to, pH and the concentrations of iron, nitrate, phosphate, and ammonia. A specific example is a commercially available Phosphate test kit, 3466, obtainable from the LaMotte Company, Chesterton, Md., USA. In this test kit, a water sample is collected and a reagent tablet is dissolved into it. A color is developed in the water sample and this color can be used to determine the concentration of the chemical species. In the present invention this colored solution, located in sensing point 92, containing the analyte 93 that reacted with the reagent tablet, can be placed into contact with the optical fiber core 106. The solution in sensing point 92 can be illuminated by a white light source 100b, or any other appropriate light with different wavelength from the side, the absorbed light is coupled into the fiber core and its intensity measured by a detector 108.

Figure 3A:
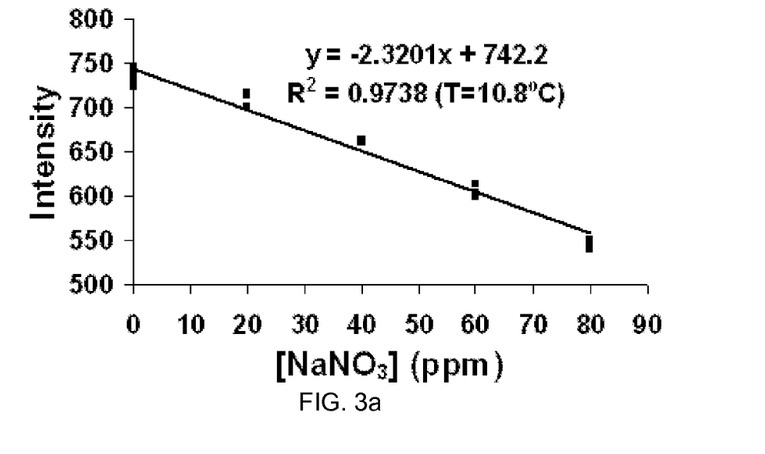
FIG. 3a is a plot of the sensor response with the concentration of sodium nitrate.

Another specific example is a commercially available Nitrate test kit, 3473, from the above-mentioned LaMotte Company. In this test kit, a water sample is collected and a nitrate reagent tablet is dissolved into it. As before, a color is developed in the water sample and the intensity of the light coupled in the fiber, due to white light illumination, is measured. The intensity of this signal against different concentrations of sodium nitrate is shown in FIG. 3a. A linear equation was fit to this data with N=50 (number of data points) and R=0.9868 (the correlation coefficient). Using the Critical Values of the Pearson Correlation Coefficient r, this correlation coefficient corresponds to a confidence level of more than 99%.

Figure 3B:
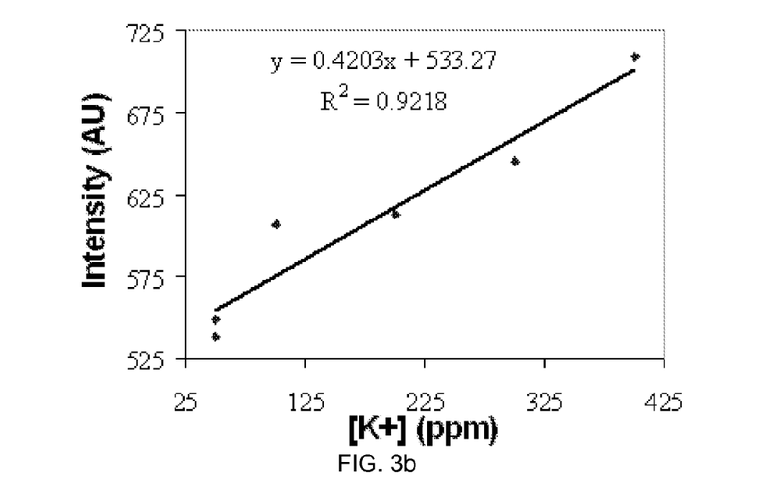
FIG. 3b is a plot of the sensor response with the concentration of Potassium ions. This curve is also a measure of the turbidity.

A turbidity meter was demonstrated with the sensor configuration of FIG. 2b. FIG. 3b is the data obtained with this configuration. In this case, turbidity was used to determine potassium ion concentration in a sample solution through the well known sodium Tetraphenylborate (TPB) method, using TPB as a reagent. Using this method, 8 mL of a 1:5 dilution ratio of different concentrations of potassium chloride (KCI) solution was mixed with two drops of sodium hydroxide reagent with metal inhibitors and 0.05 g of TPB. After the reaction between the potassium ions and the TPB occurred, the solution in sensing point 92 becomes turbid and, upon being in contact with the optical fiber core 106, it was illuminated by a white light source 100. The amount of light coupled into the optical fiber core 106, due to the light scattered by the sample in the sensing point 92, was measured with a photo detector 108a. The intensity of this signal against different concentrations of potassium ions is shown in FIG. 3b. It is to be noted that, by adding this TPB reagent to the original medium, the measurand-associated medium becomes turbid and, as the potassium ion concentration in the original medium becomes higher, the turbidity also becomes higher. As a result, the signal scattered by the solution is accordingly increased. This graph was fit with a linear curve containing 6 data points, resulting in a very high correlation coefficient R=0.96. The concentrations used were 50, 100, 200, 300 and 400 ppm of potassium ion. Using the Critical Values of the Pearson Correlation coefficient, this result corresponds to a confidence level of more than 99% (Table A-6 of Triola, 2007) (see M. F. Triola, "Elementary Statistics", 10th Edition, Pearson/Addison Wesley, 2007). This experiment was repeated a few other times resulting in similar values for the confidence level. Another way to test this turbidity sensor is by using a turbidity standard, formazin, for example, purchased in a "Formazin Calibration Kit" from Hach Company, Loveland, Colo., USA (Catalog edition dated 2008-2009).

Figure 4A:
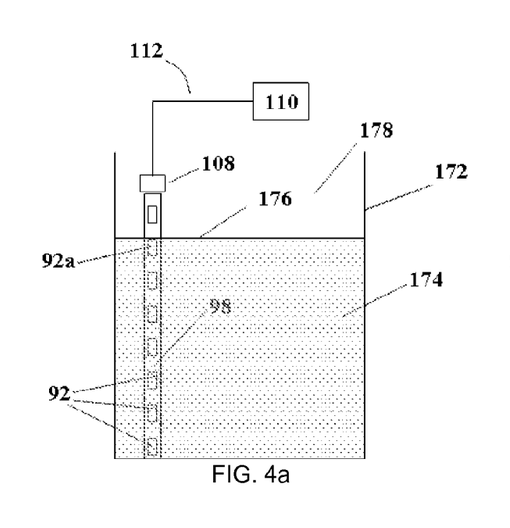
FIG. 4a is an illustration of how the sensor of FIGS. 2a and 2b can be used as a device to measure the level of a liquid or an interface between different fluids, whether a liquid or a gas. In this case, the liquid level in the fluid interface (176) is above one (92a) of the sensing points (92).
Figure 4B:
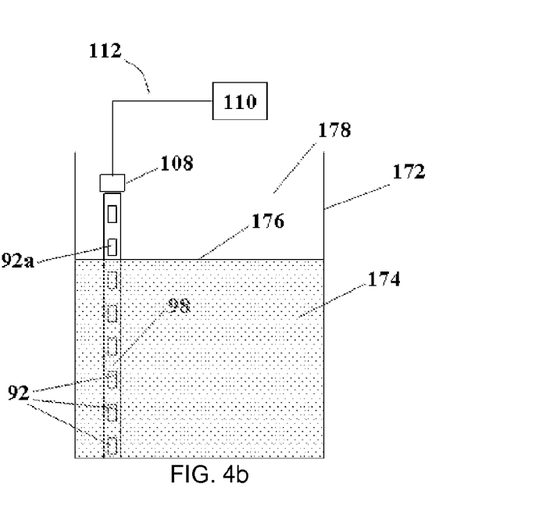
FIG. 4b is an illustration of how the sensor of FIGS. 2a and 2b can be used as device to measure the level of a liquid. In this case, the liquid level in the fluid interface (176) is below one of the sensing points (92).

The configurations of FIGS. 2a and 2b can also be used as an inexpensive refractometer to detect liquid levels inside a given enclosure. For example, referring to FIG. 2b, measurand-associated medium in sensing point 92 can be either gasoline, water or air. When the sensing point 92 is surrounded by air, the intensity read by detector 108 is, for example, 989 units. When the sensing point is surrounded by water, the intensity read is 500 units. FIGS. 4a and 4b illustrate how this sensor can be used as a liquid level sensor. FIGS. 4a and 4b show the sensing fiber 98 inside a container 172, submerged in a liquid 174 with a fluid interface 176. Above the liquid level there is air 178. The sensing fiber 98 is attached to a linear array of LEDs 138. When the sensing point, associated with the probing light source 100, is submerged in liquid 174, the signal detected by detector 108 and read by a readout 111 is lower in FIG. 4a than the signal read by the same readout in FIG. 4b. This result shows that a higher signal reading indicates that the sensing point is above the liquid level whereas a lower signal reading indicates the sensing point is below the liquid level. This procedure can be repeated to the other remaining sensing points to determine the level of the liquid.

Figure 5A:
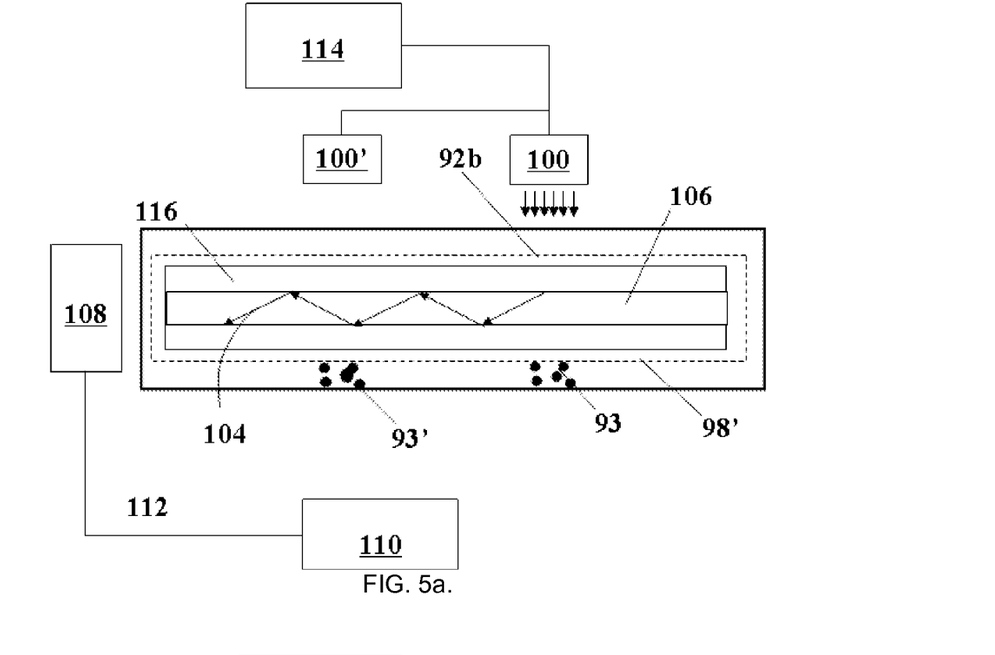
FIG. 5a is an alternate embodiment of the sensing fiber (98') with the original optical fiber cladding (116).

An alternative to the above configurations is shown in FIG. 5a. In this example, the original cladding of the sensing fiber 98' is preserved (that is, not removed) and illuminated from the outside from probing light source 100 with the fiber being surrounded by measurand-associated medium in sensing point 92. Because this configuration does not require the removal of the fiber cladding, the manufacturing of the sensor is thus simplified. This same cladded fiber can be used in conjunction with a reactive film 99 coated over the original cladding (see FIG. 5b). This reactive film has an indicator that is sensitive to the targeted species.

Figure 5B:
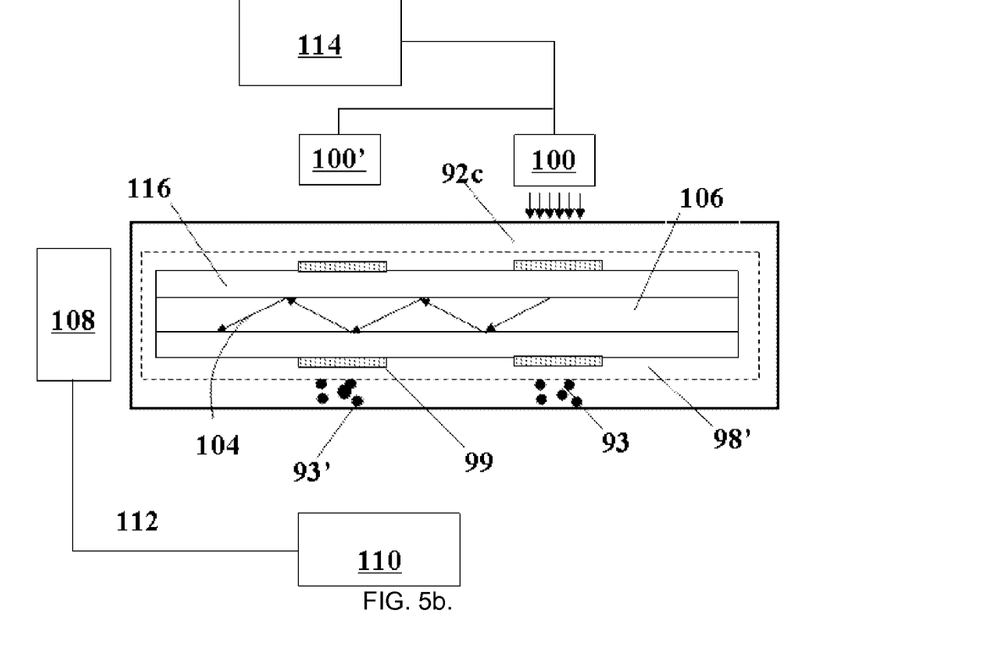
FIG. 5b is an alternate embodiment of the sensing fiber (98') with a reactive or sensitive film (99) coated over the original fiber cladding.

It is to be noted that all the fiber sensor configurations described, with the exception of FIG. 5b, do not require a chemical indicator immobilized over the fiber and is simpler than the one proposed by Egalon (U.S. Pat. No. 7,473,906).

The probing light sources of the configurations shown in FIGS. 1, 2, 5 and 8 can also be replaced by an LED containing multiple individually addressable LED dies. These LEDs can have more than one die that emit at different wavelengths and can be used to probe a single sensing point at three different wavelengths and detect more than one parameter at the sensing point.

Figure 6A:
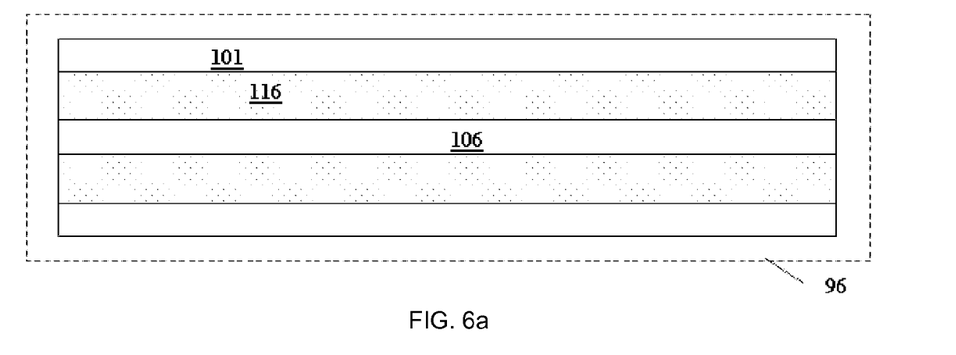
FIG. 6a is a side view of the original fiber (96).
Figure 6B:
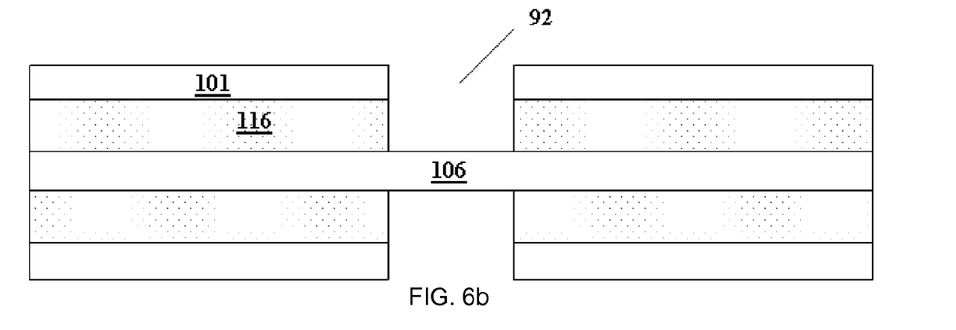
FIG. 6b is a side view of the sensing fiber, with sections of the optical fiber cladding 116 and the protective jacket 101 removed.

In all the embodiments described, there are various ways to manufacture sensing fiber 98. One of the easiest methods is to obtain a commercially available optical fiber 96*a* having an optical fiber core 106, an outer protective jacket 101 and an optical fiber cladding 116 in FIG. 6*a*). As depicted in FIG. 6*b*, the protective jacket 101 and the optical fiber cladding 116 are removed at specific positions as desired and chosen to sense the analyte (e.g., nitrate). There are several commercially available optical fibers 96 suited for this task including glass and plastic fibers. Preferably such a fiber would have a large optical fiber core 106 diameter, 1 mm to 1.5 mm, to provide the sensing fiber 98 with a high signal output, although other diameters can produce acceptable results; however, smaller and larger diameters may be employed.

Using a fiber made of a glass core 106 (e.g., see FIG. 6*a*), a plastic cladding 116, and a plastic jacket 101, sensing fiber 98 can be manufactured from the original fiber 96. This is done by removing specific sections of the plastic cladding and jacket (see FIG. 6*a*) at points where sensing is desired. The removal can be made either by chemical means, by mechanical means (using a blade), or through the use of a heat source, that burns away the protective jacket 101 and the plastic cladding 116. Through either of these methods, the glass core 106 is exposed to the outside environment. The result is the stripped region around sensing point 92 of the fiber as shown in FIG. 6*b*. Although this illustration shows a single stripped region, sensing point 92, multiple sections can be stripped away from the sensor as well, or the entire length of the optical fiber core 106 can be exposed, as desired.

Commercially available plastic optical fibers, such as Toray's Raytela® PBFU-FB1000 (Raytela® is a registered trademark of Toray Kabushiki Kaishi (Toray Industries, Inc.) Corporation) Tokyo, Japan, can also be used to create the sensor. This fiber has a plastic core and cladding, and no jacket. The cladding removal can be done by using acetone according to the procedure described in D. F. Merchant, P. J. Scully and N. F. Schmitt in "Chemical tapering of polymer optical fibre", Sensors and Actuators, vol. 76, pp. 365-371, 1999.

Figure 6C:
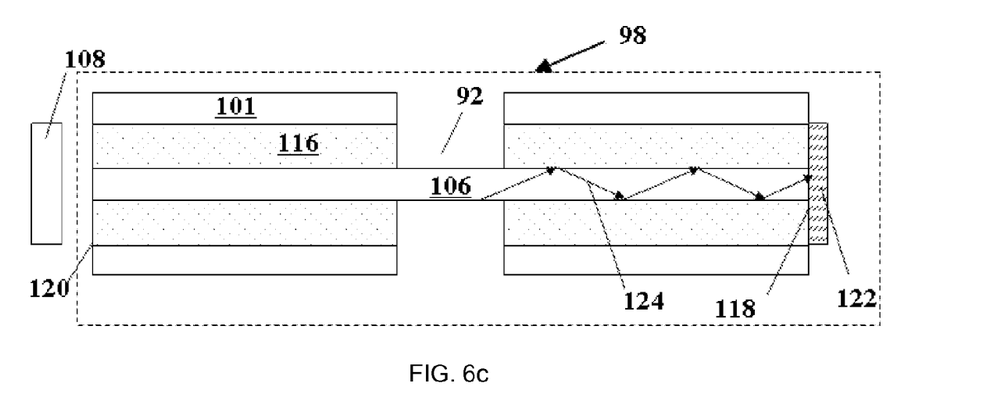
FIG. 6c is a side view of an alternate embodiment of the sensing fiber of the present invention showing a reflector (122) at the second terminus of the sensing fiber (98).

Looking at FIG. 6*c*, an additional embodiment includes a reflector 122 at the second terminus 118 of the sensing fiber 98 opposite to the detector 108, to increase the light signal through redirecting backward propagating modes 124 towards the detector 108, located at the first terminus of the fiber 120, increasing either the fluorescent, absorption or scattered based signal.

Figure 7:
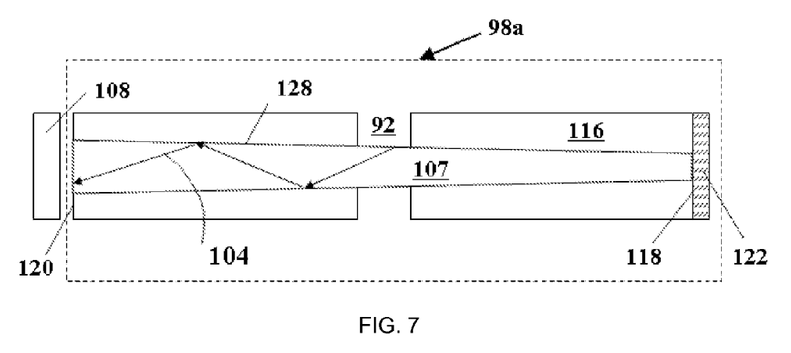
FIG. 7 is a side view of an alternate embodiment of the sensing fiber of the present invention showing a tapered core (107).

Yet another embodiment, shown in FIG. 7, includes the use of sensing fiber 98*a* with a tapered core 107, generally diverging towards the detector, as the optical signal 104 where shown propagates from the sensing point 92 to the detector 108. The interface between the tapered core and the cladding is shown to be 128. This tapered core 107 configuration has the advantage of coupling more light into the optical fiber core 106 than the other configurations and, as a result, increases the signal of the sensing fiber 98. With a tapered optical fiber core 107, light rays that otherwise would radiate away from the optical fiber core 106, are coupled as low loss bound modes, and propagate for much longer lengths. This fiber can be manufactured using a drawing tower with a tapered glass preform while it is pulled at a constant velocity. Another method is to pull a regular cylindrical preform at varying velocities to create the taper in the fiber. Alternatively, this fiber can also be manufactured manually by those skilled in the shaping of glass. Another way is to taper an plastic optical fiber using the procedure outlined by Merchant et al., referenced above.

Figure 8:
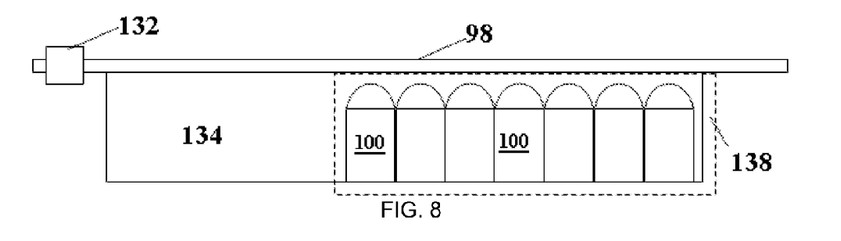
FIG. 8 is a side view of an alternate embodiment of the sensing fiber of the present invention, showing a linear array (138) of LEDs (100a).

In yet another embodiment, as seen in FIG. 8, a plurality of light sources, such as UV LEDs 100, are mounted inside an optical fiber support 134 in a linear array along the length of the sensing fiber 98, with each probing light source 100 simultaneously emitting an excitation light towards the optical fiber core 106 (see FIGS. 1*a*, 1*b*, 1*c*, 2*a*, 2*b*, 5*a* and 5*b*). The length of the linear array of LEDs 138 corresponds substantially to the length of the sensing point 92 of the sensing optical fiber 98 (also as shown in FIGS. 1*a*, 1*b*, 1*c*, 2*a*, 2*b*, 5*a* and 5*b*). This arrangement can be used to increase the overall signal of the sensing fiber 98. An optical fiber connector 132 provides protection to the end of the sensing fiber 98, preventing breakage, and allows a reproducible positioning of the end of the sensing fiber 98 next to the detector 108 (e.g., also see FIGS. 1*a*, 1*b*, 1*c*, 2*a*, 2*b*, 5*a* and 5*b*). By alternately turning on and off each LED 100, it is possible to probe a specific sensing point 92, resulting in an enhanced distributed sensing fiber 98.

The power supply 114 (see FIGS. 1*a*, 1*b*, 1*c*, 2*a*, 2*b*, 5*a* and 5*b*) is preferably designed in such a way that it does not exceed the current limitations of the LEDs 100*a*. Commercially available LED drivers can be used as a power supply for the source such as Sandhouse Design's LED-PS (Sandhouse Design LLC, Dunedin, Fla., USA).

Figure 9A:
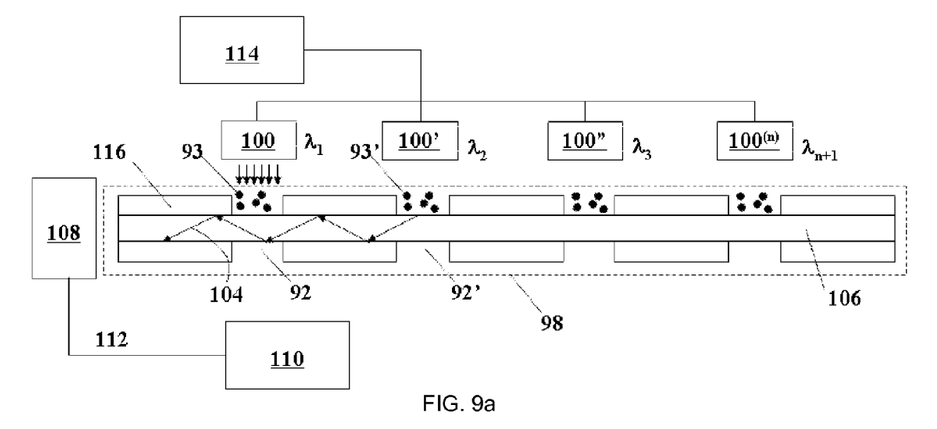
FIG. 9a is an illustration of a simple spectrometer-like device that uses several sensing points (92, 92', 92", . . . ).

FIG. 9*a* is an illustration of a simple spectrometer-like device that uses several sensing points (92, 92', 92", . . . ) of the side illuminated sensitive optical fiber (98) with and a detector (108) to determine a given analyte (93) in the sensing points (92). Each sensing point (92) is illuminated by their corresponding probing light source (100, 100', . . . ) having different peak wavelengths, $\lambda_i$. When each of these sensing points is probed, one at a time, the detector reads the signal of the lit light source (100). By mapping the response of the sensor to each source of different peak wavelength, due to the absorption of the analyte (93), we have a very inexpensive device that works like a simple spectrometer. The resolution of this spectrometer-like device depends on the bandwidth of the wavelength, $\Delta\lambda_i$, of each probing light source (100).

Figure 9B:
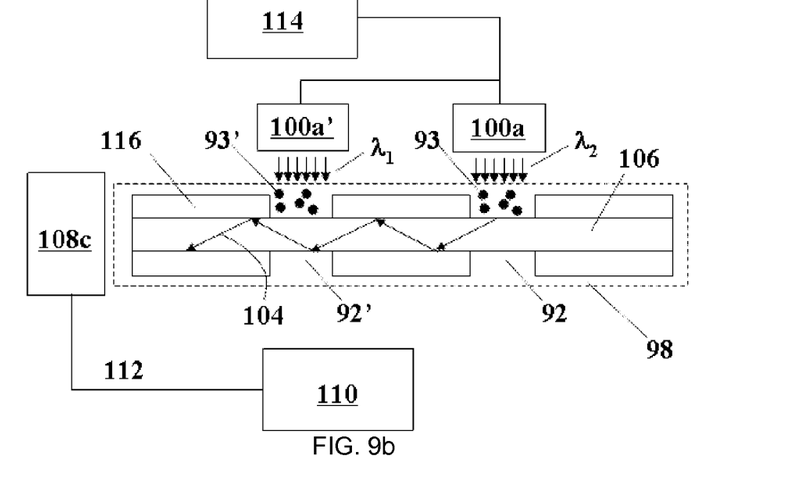
FIG. 9b is a side view of an alternate embodiment of the sensing fiber (98) of the present invention showing two LEDs (100a and 100a') simultaneously lighting different sensing points (92).

FIG. 9*b* is an illustration of an alternate embodiment where the sensing fiber (98) has at least 2 sensing points (92) that are simultaneously illuminated by their corresponding LEDs (100*a*). These LEDs have different wavelengths which allows for the simultaneous determination of the measurands being probed at their corresponding sensing points with a spectrometer (108*c*) located at the first terminus of the optical fiber (120).

In addition to the previously described embodiments, alternative embodiments of these illumination schemes are possible. For example, the LEDs 100*a* may be replaced with a strip of OLEDs (Organic Light Emitting Diodes). Such OLEDs can be incorporated into a strip over which the optical fiber sensor is mounted.

Figure 10A:
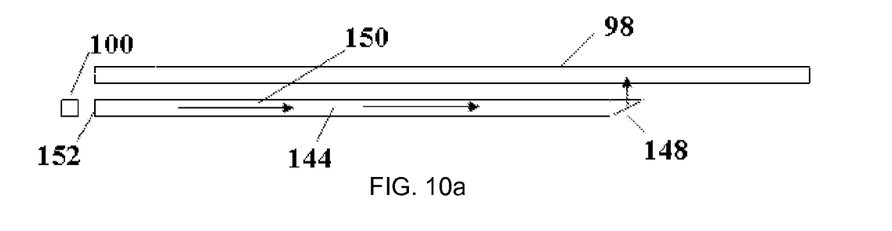
FIG. 10a is an illustration showing the operation of an illumination optical fiber with a 45 degrees distal end. The light from the probing light source (100) is injected axially.

FIG. 10*a* shows an alternate embodiment that uses an illumination optical fiber 144 to probe the sensing point 92 (see FIGS. 2*a* and 2*b*) of the sensing fiber 98. In this case, the illumination optical fiber 144 serves as a light guide for the illumination light 150 and the illumination optical fiber 144 is deployed parallel to sensing fiber 98. The illumination optical fiber 144 includes a reflecting distal end face 148 at an angle of approximately 45 degrees, although other angles may also be employed, which redirects the illumination light 150 towards the sensing region of the sensing fiber 98. However, angles other than 45 degrees are employable provided that the light is directed towards the sensing region. In this embodiment, the illumination light is generated by a probing light source 100 at the proximal end of the fiber 152, and introduced axially. The position of the reflecting distal end face 148 can be changed to probe different sections of the sensing fiber 98 or multiple illumination fibers can be used, each probing a specific area of the sensing fiber 98.

Figure 10B:
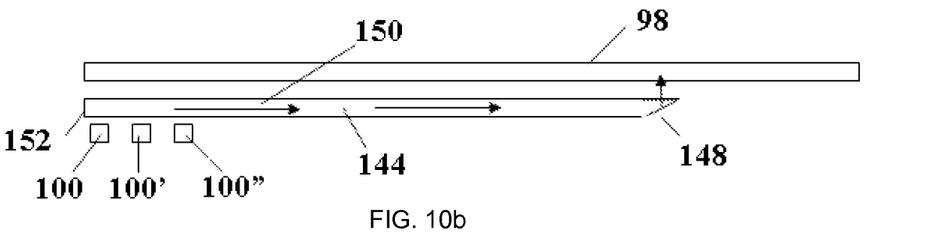
FIG. 10b is an illustration showing the operation of an illumination optical fiber with a 45 degrees distal end. The light from the probing light source (100, 100', 100") is injected in the side of the optical fiber allowing an N×1 coupler configuration with a single fiber.

FIG. 10*b* illustrates an alternative embodiment of FIG. 10*a* where multiple probing light sources, 100, 100', 100", etc., side illuminate the optical fiber 144. This is a preferred configuration because it allows for multiple simultaneous illumination of the optical fiber 144 from different light sources. It also simplifies the illumination fiber because it does not require precise alignment of the sources nor the use of lenses to focus the light into the small proximal end of the fiber 152. For this specific configuration, the illumination optical fiber 144 should preferably be illuminated at a point where there is no cladding. The illumination of optical fiber 144 is effected in a similar way as the illumination of the sensing fiber 98. Also, in this case, the illumination optical fiber 144 also acts as a simple N×1 coupler that requires a single fiber.

Figure 11A:
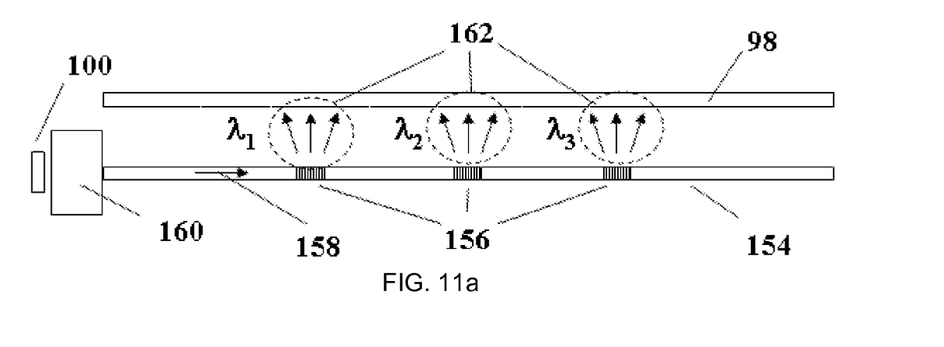
FIG. 11a is an illustration showing the operation of an illumination optical fiber made of several long period Bragg gratings. The light is injected axially.
Figure 11B:
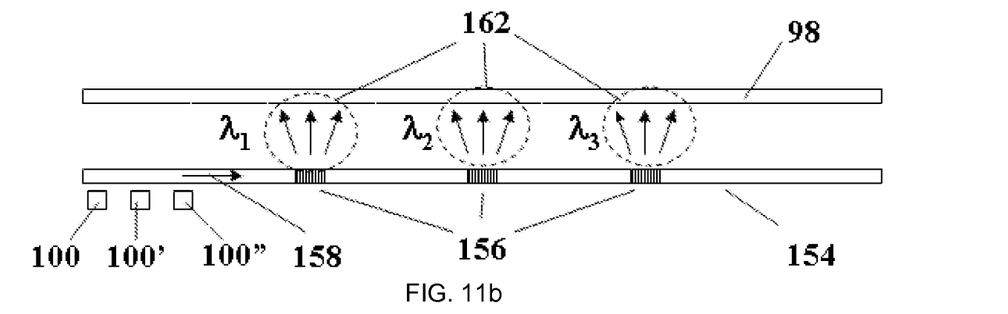
FIG. 11b is an illustration showing the operation of an illumination optical fiber made of several long period Bragg gratings. The light is injected in the side of the optical fiber allowing an N×1 coupler configuration with a single fiber.

Yet another alternate embodiment, as seen in FIG. 11*a*, uses an illumination optical fiber 154 having several long period gratings 156. This illumination fiber 154 is also deployed along the sensing fiber 98 and illuminates several of its sections through the long period gratings 156. Each long period grating 156 is designed to couple light from a bound mode core 158 of the illumination optical fiber 154 into radiation modes 162 at specific wavelengths, $\lambda_i$, within the absorption spectrum of the sensing region. In this case, the light from a broadband probing light source 100 passes through a monochromator 160 that scans the wavelengths within the absorption spectrum of the sensing region of the sensing fiber 98. When the monochromator 160 is tuned to a wavelength $\lambda_i$, only the specific long period grating 156 tuned to this wavelength couples the light towards the sensing fiber 98, and the illuminated section corresponds to the position of this specific long period grating 156. The procedure can be repeated for other wavelengths. The same procedure as outlined in FIG. 11*b* can be used for the configuration as shown in FIG. 11*a* where the probing light sources 100, 100' and 100" are placed in the side of the illumination fiber (see FIG. 11*b*). In this case, each probing light source 100, 100' and 100" can be chosen to be sources of different peak wavelengths that are tuned to the gratings in illumination fiber 154.

Figure 12A:
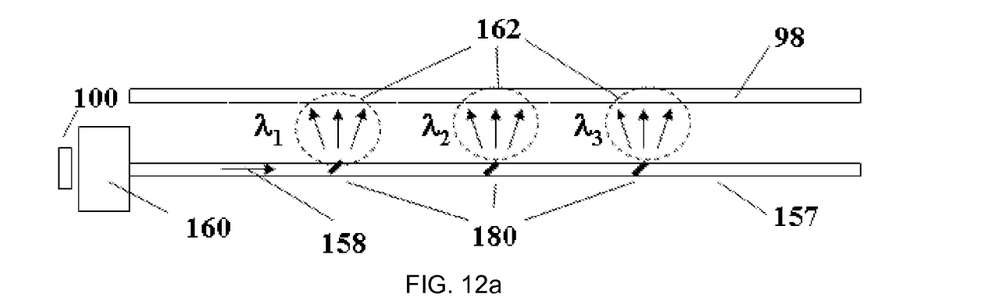
FIG. 12a is an illustration showing the operation of an illumination optical fiber made of several embedded dielectric mirrors 180. The light is injected axially.
Figure 12B:
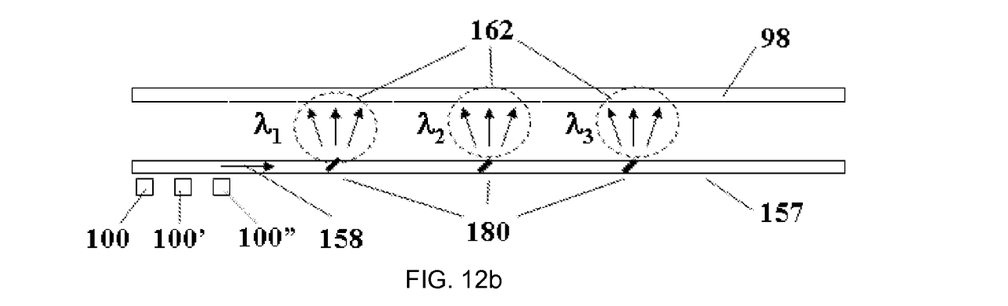
FIG. 12b is an illustration showing the operation of an illumination optical fiber made of several embedded dielectric mirrors 180. The light is injected in the side of the optical fiber allowing an N×1 coupler configuration with a single fiber.

Two more embodiments of an illumination fiber are illustrated in FIGS. 12*a* and 12*b* for axial and side illumination, respectively. In this case, the illumination fiber 157 is manufactured with several embedded dielectric mirrors 180, with each being positioned at an angle of 45 degrees. Each embedded dielectric mirror is designed to reflect light at a specific wavelength, $\lambda_i$, (e.g., $\lambda_1$, $\lambda_2$ and $\lambda_3$), from a bound mode into a radiation mode of the illumination fiber, towards the sensing point 92 of the sensing fiber 98. This fiber works similarly to the illumination fiber made of Bragg gratings with the advantage that it is cheaper to produce. These wavelengths, $\lambda_i$, are within the absorption spectrum of the measurand-associated medium in the sensing point 92 (see FIGS. 1*a*, 1*b* and 1*c*) surrounding the sensing fiber 98. By varying the wavelength of the input light, it is possible to probe multiple points, at known locations, along the fiber sensor, thus creating an enhanced distributed sensing system.

In both cases of FIGS. 11*a* and 12*a*, the monochromator can be replaced by multiple monochromatic light sources such as LEDs and lasers.

Figure 13:
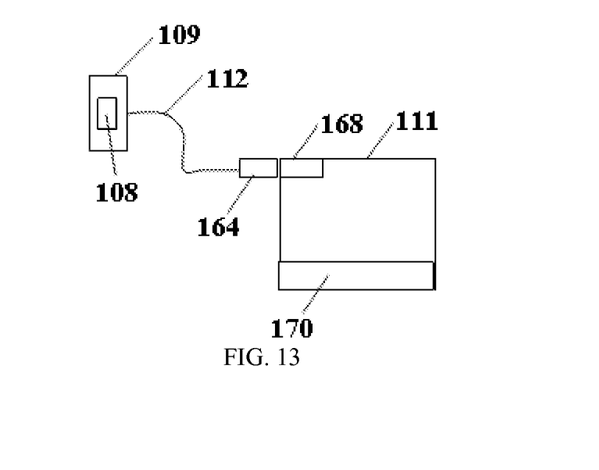
FIG. 13 is a block diagram of the detection system of the present invention.

An embodiment of the detection system is shown in FIG. 13, comprising a silicon photodetector 108 inside a light-tight enclosure 109, a photodetector cable 112, a male connector 164 and a read out 111. The male connector 164 is connected to a female connector 168 in the read out 111. The photodetector 108 is mounted inside a light tight enclosure 109 which can be connected to the optical fiber connector shown in FIG. 8. The leads of the detector are connected to a cable that transmits the photo-electric signal to an amplification circuit. The circuit amplifies the signal and its intensity is displayed in the display 170 of the read out 111. There are several commercially available detection systems that can be used with the current art, such as AEMC's Instruments Lightmeter Model CA811, (Chauvin Arnoux®, Inc. d.b.a. AEMC® Instruments, Foxborough, Mass., USA, Hamamatsu Corporation's Photodiode Module C10439 (Hamamatsu Photonics, K.K., headquartered in Hamamatsu City, Japan and having a subsidiary, Hamamatsu Corporation, Bridgewater, N.J., USA), and Sandhouse Design's Single Point Detector Model No. SPD-UVNIS (Sandhouse Design, Bridgewater, N.J.).

The present invention, in its various forms, can be used in many different applications, including but not limited to, monitoring the turbidity and color of a solution, the concentration of chlorophyll, the level of a liquid and others.

While the present invention has been described with regards to particular embodiments, it is recognized that additional variations of the present invention may be devised without departing from the inventive concept. Many improvements, modifications, and additions will be apparent to the skilled artisan without departing from the spirit and scope of the present invention as described herein and defined in the following claims.

Reference Numerals

| | |
|---|---|
| 92 | Sensing point, Exposed core region |
| 92a | Specific sensing point |
| 93 | Analyte, measurand medium |
| 96 | Original optical fiber |
| 98 | Sensing fiber, sensitive optical fiber |
| 98a | Optical fiber sensor with a tapered core |
| 99 | Reactive film, Sensitive film |
| 100 | Probing light source |
| 100a | LED |
| 100b | White light source |
| 101 | Protective jacket |
| 101a | Plastic jacket |
| 104 | Optical signal |
| 104a | Fluorescence |
| 106 | Optical fiber core, core |
| 106a | Glass core |
| 107 | Tapered core |
| 108 | Detector |
| 108c | Spectrometer |
| 109 | Light tight enclosure |
| 110 | Signal processor |
| 111 | Readout |
| 112 | Photodetector cable |
| 114 | Power Supply |
| 116 | Optical fiber cladding |
| 118 | Second terminus of the optical fiber |
| 120 | First terminus of the optical fiber |
| 122 | Reflector |
| 124 | Backward propagating modes |
| 128 | Interface between tapered core and cladding |
| 132 | Optical fiber connector |
| 134 | Optical fiber support |

| | |
|---|---|
| 138 | Linear array of LEDs |
| 144 | Illumination optical fiber |
| 148 | Reflecting distal end face |
| 150 | Illumination light |
| 152 | Proximal end of the fiber |
| 154 | Illumination optical fiber with several long period gratings |
| 156 | Long period gratings |
| 160 | Monochromator |
| 162 | Radiation modes |
| 164 | Male connector of the photodetector |
| 168 | Female connector of the read out unit |
| 170 | Display |
| 172 | Container |
| 174 | Liquid |
| 176 | Fluid interface |
| 178 | Air |
| 180 | Embedded dielectric mirror |

It is claimed:

1. An optical analytic subsystem comprising:
a sensing optical fiber having at least one exposed core region free of cladding and free of sensitive coating or other sensitive, reactive chemical preparation;
at least one light source, each having a respective, predetermined output spectrum, the at least one light sources respectively associated with one of the at least one exposed core regions such that energizing the light source engenders a probing light to be transversely directed to side-illuminate the associated exposed core region from outside of the sensing fiber;
at least one location, the at least one locations respectively associated with one of the at least one exposed core regions, and at least one of the light sources, the location being adapted to accept inclusion of an analyte, and where the location is positioned relative to the associated exposed core region and to the associated light source's probing light path that, where the analyte has at least one of the properties of the list: chemiluminescence, phosphorescence, fluorescence, scattering, refraction, reflection and absorption, of light at the associated light source's spectrum, the probing light is modified such that a resultant light signal is coupled into the sensing fiber's core and is detectable at a terminus of the sensing fiber such as to identify a measurand of the analyte.

2. The optical analytic subsystem of claim 1 where the at least one exposed core region, the at least one location, and the at least one light source are at least two exposed core regions, at least two locations, and at least two respective light sources; and further comprises a circuit configured to energize the light sources in a predetermined sequence.

3. The optical analytic subsystem of claim 2 where the light source energization sequencing is serial.

4. The optical analytic subsystem of claim 2 where the light source energization sequencing is substantially simultaneous.

5. The optical analytic subsystem of claim 2 where the fiber's core is tapered.

6. The optical analytic subsystem of claim 1 where at least one of the at least one light sources emits light in the far infrared spectrum.

7. The optical analytic subsystem of claim 1 where at least one of the at least one light sources is an UV LED.

8. The optical analytic subsystem of claim 1 where the fiber is plastic.

9. The optical analytic subsystem of claim 1 further comprising a photodiode, a photodiode amplifier, and a light source power supply.

10. The optical analytic subsystem of claim 9 further comprising a display and a signal processor in mutual communication, and the signal processor in operative communication with the photodiode; the display and signal processor configured to provide indication of the degree of a measurand of a substance that is disposed at one of the at least one locations.

11. The optical analytic subsystem of claim 10 in which the measurand comprises the identity of at least a portion of the composition of the substance.

12. The optical analytic subsystem of claim 10 in which the measurand comprises at least one of color, turbidity, and refractive index.

13. The optical analytic subsystem of claim 10 in which the at least one exposed core region is at least two distinct exposed core regions.

14. The optical analytic subsystem of claim 13 where the subsystem is configured such that the at least two exposed core regions are individually illuminated.

15. The optical analytic subsystem of claim 13 where the subsystem is configured such that the at least two exposed core regions are simultaneously illuminated.

16. The optical analytic subsystem of claim 13 where the at least two exposed core regions are at least three exposed core regions and where the subsystem is configured such that the at least three exposed core regions are illuminated sequentially in the order the regions occur along the fiber.

17. The optical analytic subsystem of claim 10 where the fiber optic, including both core and any cladding, are tapered.

18. An optical analytic subsystem comprising:
a fiber optic configured to receive light that side illuminates the fiber at least at one exposed core region free of cladding and free of sensitive coating or other sensitive, reactive chemical preparation and configured to guide said light to at least one of its termini;
at least one light source positioned and oriented to illuminate the side of said fiber optic at the at least one exposed core region and where the fiber optic is tapered proximate to at least one of the at least one exposed core regions.

19. The optical analytic subsystem of claim 1 where the optical sensing fiber is free of any core region comprising sensitive coating or other sensitive, reactive chemical preparation attached to the sensing fiber at an operational position.

* * * * *